United States Patent
Daussin et al.

(10) Patent No.: US 10,168,244 B2
(45) Date of Patent: Jan. 1, 2019

(54) GASEOUS FUEL MONITORING FOR WELLSITE PUMPS

(71) Applicant: Halliburton Energy Services, Inc., Houston, TX (US)

(72) Inventors: Rory D. Daussin, Houston, TX (US); Neal G. Skinner, Carrollton, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 228 days.

(21) Appl. No.: 15/036,610

(22) PCT Filed: Feb. 14, 2014

(86) PCT No.: PCT/US2014/016466
§ 371 (c)(1),
(2) Date: May 13, 2016

(87) PCT Pub. No.: WO2015/122906
PCT Pub. Date: Aug. 20, 2015

(65) Prior Publication Data
US 2016/0290890 A1     Oct. 6, 2016

(51) Int. Cl.
*G01M 3/38* (2006.01)
*E21B 41/00* (2006.01)
(Continued)

(52) U.S. Cl.
CPC ........... *G01M 3/38* (2013.01); *E21B 41/0085* (2013.01); *G01F 1/6845* (2013.01);
(Continued)

(58) Field of Classification Search
CPC ..... G01M 3/38; G01M 3/002; E21B 41/0085; G01F 1/6845; G01J 5/0014
See application file for complete search history.

(56) References Cited

U.S. PATENT DOCUMENTS 5,013,111 A * 5/1991 Tilly .................... G02B 6/4202
                                                              372/36
5,235,666 A * 8/1993 Ooe ........................ C03C 13/045
                                                              385/144
(Continued)

FOREIGN PATENT DOCUMENTS

WO    WO-2015/122906 A1    8/2015

OTHER PUBLICATIONS

"International Application Serial No. PCT/US2014/016466, Written Opinion dated Nov. 7, 2014", 9 pgs.
(Continued)

*Primary Examiner* — Lisa Caputo
*Assistant Examiner* — Philip Cotey
(74) *Attorney, Agent, or Firm* — Chamberlain Hrdlicka (57) ABSTRACT

A gaseous fuel monitoring system can include a gaseous fuel supply enclosure, an optical line extending along the gaseous fuel supply enclosure, and a relatively highly thermally conductive material contacting both the gaseous fuel supply enclosure and the optical line. The relatively highly thermally conductive material can comprise a pyrolytic carbon material. A method of detecting leakage from a gaseous fuel supply enclosure can include securing an optical line to the gaseous fuel supply enclosure, the securing comprising contacting a pyrolytic carbon material with the optical line and the gaseous fuel supply enclosure. A gaseous fuel monitoring system can include an optical interrogator connected to the optical line, which interrogator detects changes in light transmitted by the optical line due to changes in vibrations of the enclosure.

20 Claims, 3 Drawing Sheets

(51) Int. Cl.
*G01F 1/684* (2006.01)
*G01J 5/00* (2006.01)
*G01M 3/00* (2006.01)
*G01N 21/17* (2006.01)
*E21B 33/13* (2006.01)
*E21B 43/26* (2006.01)

(52) U.S. Cl.
CPC .......... *G01J 5/0014* (2013.01); *G01M 3/002* (2013.01); *G01N 21/1702* (2013.01); *E21B 33/13* (2013.01); *E21B 43/26* (2013.01); *G01N 2021/1704* (2013.01); *G01N 2201/08* (2013.01)

(56) References Cited

U.S. PATENT DOCUMENTS

| | | | | |
|---|---|---|---|---|
| 5,256,177 | A * | 10/1993 | Bennett | C03C 25/223 427/109 |
| 6,350,033 | B1 * | 2/2002 | Fujimori | G03B 21/16 353/119 |
| 7,033,443 | B2 * | 4/2006 | Kellerman | C23C 16/4586 118/724 |
| 7,191,832 | B2 | 3/2007 | Grigsby et al. | |
| 7,357,021 | B2 | 4/2008 | Blacklaw | |
| 8,505,625 | B2 | 8/2013 | Ravi et al. | |
| 2002/0154860 | A1 * | 10/2002 | Fernald | G01L 11/025 385/37 |
| 2004/0168521 | A1 * | 9/2004 | Andersen | E21B 47/0006 73/807 |
| 2004/0187788 | A1 * | 9/2004 | Kellerman | C23C 16/4586 118/728 |
| 2004/0234221 | A1 * | 11/2004 | Kringlebotn | C03C 25/104 385/128 |
| 2005/0260468 | A1 | 11/2005 | Fripp et al. | |
| 2009/0114386 | A1 * | 5/2009 | Hartog | E21B 43/26 166/250.08 |
| 2010/0046896 | A1 * | 2/2010 | Mahapatra | G02B 6/443 385/114 |
| 2010/0269941 | A1 | 10/2010 | Hara | |
| 2010/0303104 | A1 * | 12/2010 | Bennetts | G02B 6/14 372/6 |
| 2011/0043799 | A1 * | 2/2011 | Mitani | G01N 21/552 356/300 |
| 2011/0088462 | A1 | 4/2011 | Samson et al. | |
| 2011/0090496 | A1 | 4/2011 | Samson et al. | |
| 2011/0194107 | A1 | 8/2011 | Hartog et al. | |
| 2011/0215936 | A1 | 9/2011 | Ansari et al. | |
| 2011/0320147 | A1 | 12/2011 | Brady et al. | |
| 2012/0014211 | A1 | 1/2012 | Maida, Jr. et al. | |
| 2012/0222770 | A1 * | 9/2012 | Kristiansen | F16L 11/08 138/103 |

OTHER PUBLICATIONS

"International Application Serial No. PCT/US2014/016466, International Search Report dated Nov. 7, 2014", 3 pgs.

* cited by examiner

GASEOUS FUEL MONITORING FOR WELLSITE PUMPS

PRIORITY APPLICATIONS

This application is a U.S. National Stage Filing under 35 U.S.C. 371 from International Application No. PCT/US2014/016466, filed on 14 Feb. 2014, and published as WO 2015/122906 A1 on 20 Aug. 2015, which application and publication are incorporated herein by reference in their entirety.

TECHNICAL FIELD

This disclosure relates generally to equipment utilized and operations performed in conjunction with a subterranean well and, in one example described below, more particularly provides for gaseous fuel monitoring for wellsite pumps.

BACKGROUND

In some situations, wellsite pumps (such as, those used for fracturing, conformance or cementing operations, etc.) may be powered by motors utilizing liquid and/or gaseous fuels. It would be beneficial to be able to detect leakage of any gaseous fuel at a wellsite, and/or to detect characteristics of the gaseous fuel flow, in order to enhance safety, efficiency, etc., of such wellsite operations.

DETAILED DESCRIPTION

Figure 1:
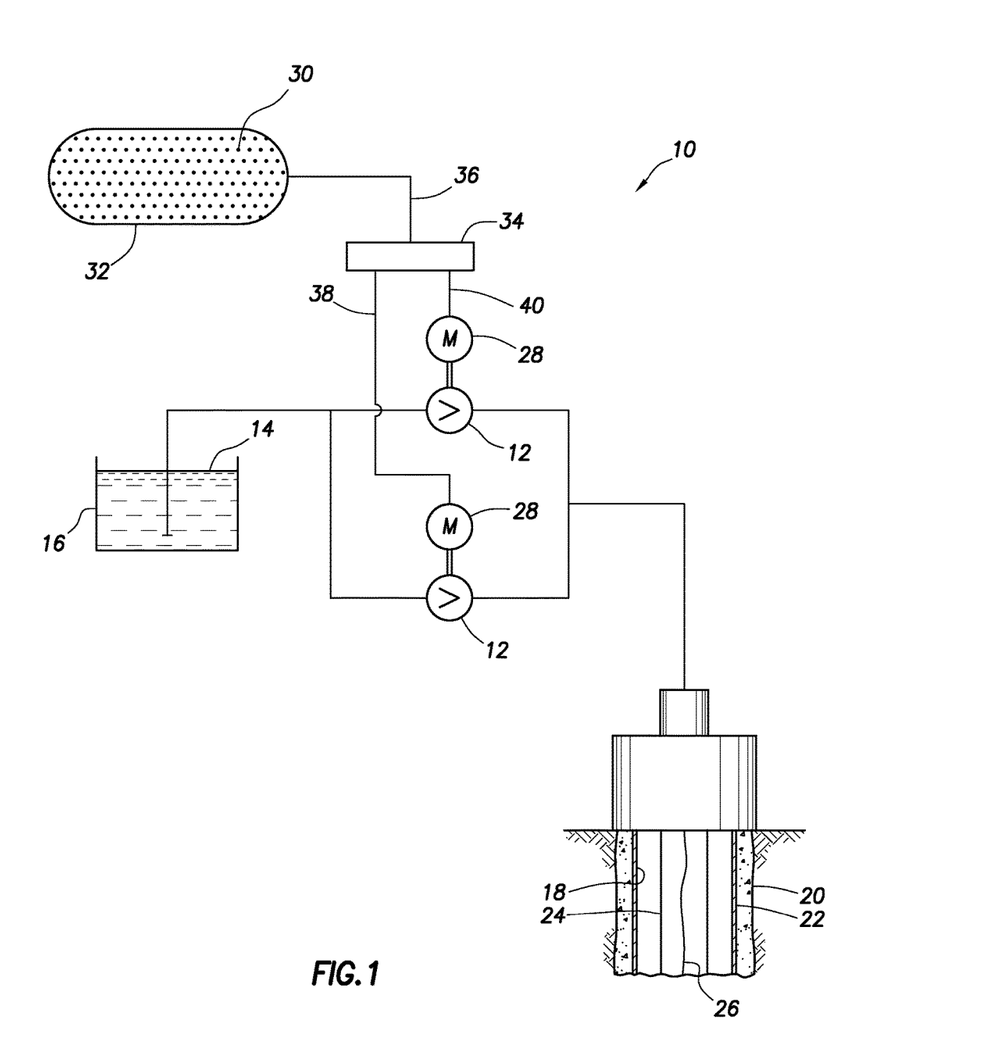
FIG. 1 is a representative partially cross-sectional view of a well system and associated method which can embody principles of this disclosure.

Representatively illustrated in FIG. 1 is a system 10 for use with a well, and an associated method, which can embody principles of this disclosure. However, it should be clearly understood that the system 10 and method are merely one example of an application of the principles of this disclosure in practice, and a wide variety of other examples are possible. Therefore, the scope of this disclosure is not limited at all to the details of the system 10 and method described herein and/or depicted in the drawings.

In the FIG. 1 example, pumps 12 are used to pump a fluid 14 into a wellbore 18 from a reservoir 16 at the earth's surface. The fluid 14 could be a fracturing fluid, a conformance fluid, cement, a slurry (such as, a gravel slurry, proppant slurry, cement slurry, etc.), combinations of fluids and gels and/or particulate material, etc. Thus, it should be clearly understood that the scope of this disclosure is not limited to pumping of any particular type of fluid or other material.

As depicted in FIG. 1, the wellbore 18 is lined with cement 20 and casing 22. A tubular string 24 (such as, a tubular work string, completion string, etc.) is used as a conduit to flow the fluid 14 into the wellbore 18, and to a desired location therein. In other examples, the tubular string 24 may not be used, the wellbore 18 may not be cased or cemented at a location to which the fluid 14 is pumped, etc. Thus, the scope of this disclosure is not limited to any details of the wellbore 18 or tubular string 24 depicted in the drawings or described herein.

An optical line 26 can extend in the wellbore 18, for example, to monitor the pumping of the fluid 14. Optical systems capable of such fluid flow monitoring are described in U.S. Pat. Nos. 7,191,832, 7,357,021 and 8,505,625, and in U.S. Publication Nos. 2011-0090496, 2011-0088462 and 2012-0014211. In addition, distributed temperature sensing (DTS) systems for use in wells are well known to those skilled in the art.

The optical line 26 can comprise one or more optical fibers, or other types of optical waveguides (such as, optical ribbons, etc.). The optical line 26 can be in the form of a cable or a tubing having the optical waveguide(s) therein. The optical waveguide(s) may be accompanied by electrical, hydraulic or other types of lines or conduits.

The optical line 26 may be positioned internal or external to the tubular string 24, or internal or external to the casing 22, or in a wall of the tubular string or casing. Thus, the scope of this disclosure is not limited to any particular type, configuration or position of the optical line 26, or to use of the optical line in the wellbore 18 at all.

Motors 28 (such as, internal combustion engines, turbines, etc.) are used to provide power to the pumps 12. In some examples, liquid fuel (such as, gasoline or diesel fuel) may be combusted by the motors 28. In the FIG. 1 example, the motors 28 also, or alternatively, combust a gaseous fuel 30. The gaseous fuel 30 may comprise natural gas, methane, propane, butane, or any other suitable gaseous fuel (or mixture of gaseous fuels).

As depicted in FIG. 1, the gaseous fuel 30 is transported and stored in a supply tank 32. The fuel 30 flows from the tank 32 to a manifold 34 via a gas line 36. The fuel 30 is distributed from the manifold 34 to the individual motors 28 via gas lines 38, 40.

Note that the distribution of the gaseous fuel 30 to the motors 28 as shown in FIG. 1 is merely schematic, since additional or different equipment may be used in keeping with the principles of this disclosure. For example, various valves and control systems can be used to control flow of the fuel 30, use of the manifold 34 is not necessary, any number of motors 28 may be supplied with the fuel, etc. Thus, the scope of this disclosure is not limited to any details of the gas distribution system depicted in FIG. 1 or described herein.

The gaseous fuel supply tank 32, gas lines 36, 38, 40 and manifold 34 are examples of enclosures from which the gaseous fuel 30 could leak and thereby cause a potentially hazardous situation. Therefore, it would be beneficial to be able to promptly detect a leak of the gaseous fuel 30 from any of these enclosures proximate the earth's surface. As used herein, "proximate the earth's surface" includes locations at or near ground level, as well as on a body of water, but not downhole or in a wellbore.

Figure 2:
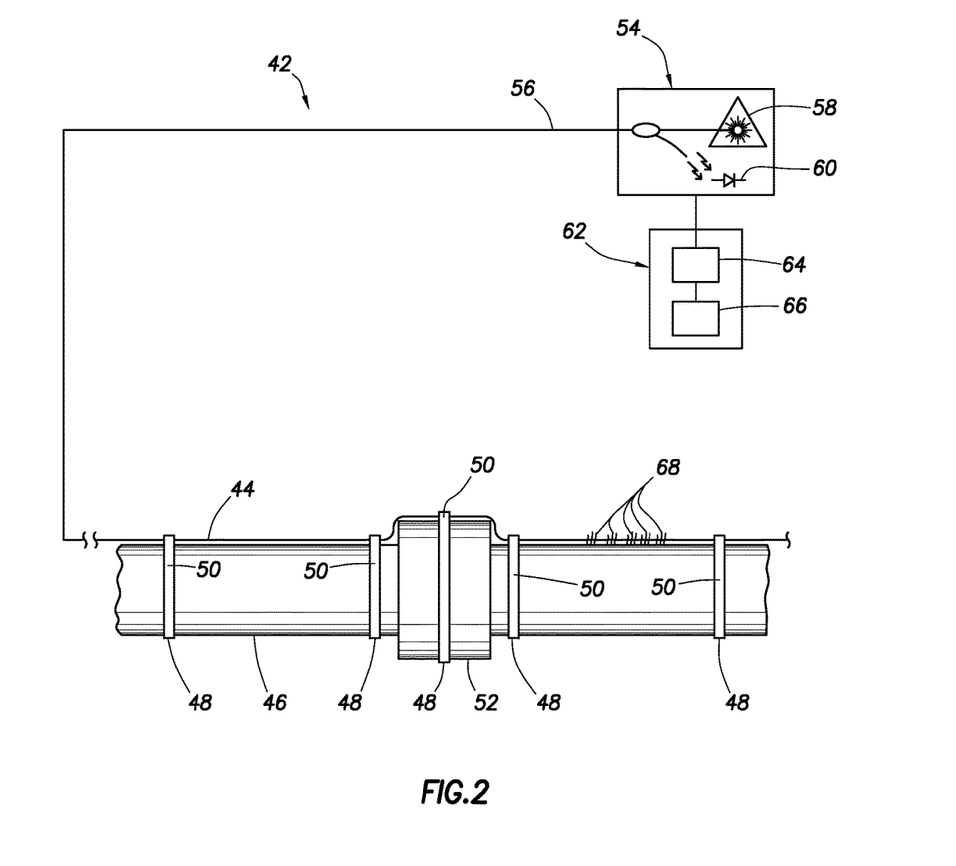
FIG. 2 is a representative view of a gaseous fuel monitoring system and method which can be used with the well system and method of FIG. 1, and which can embody the principles of this disclosure.

Referring additionally now to FIG. 2, an example of a gaseous fuel monitoring system 42 that may be used with the system 10 of FIG. 1 is representatively illustrated. Of course, the monitoring system 42 can also be used with other well systems and methods, in keeping with the principles of this disclosure.

In the FIG. 2 example, an optical line 44 extends along a gaseous fuel enclosure 46. The enclosure 46 may be a flexible or rigid conduit, pipe or tubing (such as, the gas lines

36, 38, 40), a tank (such as, the supply tank 32), a manifold (such as, the manifold 34), or any other type of structure in which the gaseous fuel 30 is contained.

The optical line 44 extends relatively straight longitudinally along the enclosure 46 as depicted in FIG. 2. However, in other examples, the optical line 44 could extend helically about the enclosure 46, in a zig-zag pattern, or otherwise along the enclosure. Thus, the scope of this disclosure is not limited to any particular manner of extending the optical line 44 along the enclosure 46.

The optical line 44 is secured to the enclosure 46 so that, if the gaseous fuel 30 leaks from the enclosure, a temperature change of the enclosure will result in a temperature change of the optical line. In the FIG. 2 example, clamps 48 are used to secure the optical line 44 closely to the enclosure 46.

A temperature change can result from leakage of the gaseous fuel 30, due to the well-known Joule-Thomson effect. In basic terms, a gas cools as it expands. The temperature change can be expressed by the following equation:

$$\Delta T = \mu_{JT} * \Delta P \qquad (1)$$

wherein $\Delta T$ is the temperature change, $\Delta P$ is a change in pressure, and $\mu_{JT}$ is a Joule-Thomson coefficient dependent on certain properties of the gas.

In a leakage situation, the gaseous fuel 30 will cool as it leaks from the enclosure 46, thereby causing the enclosure to be cooled at a location of the leak. A suitable heat transfer mechanism between the enclosure 46 and the optical line 44 will desirably result in the optical line also being cooled at the location of the leak. Such cooling of the optical line 44 (and one or more optical waveguides therein) can be detected by an optical distributed temperature sensing (DTS) system.

In the FIG. 2 example, efficient heat transfer between the optical line 44 and the enclosure 46 is provided by coating the clamps 48 with a relatively highly thermally conductive material 50. One suitable material is pyrolytic carbon or pyrolytic graphite, which has a thermal conductivity of about 1700 W/m° K, more than eight times that of aluminum, and more than four times that of copper. The highly thermally conductive material 50 preferably has a thermal conductivity of at least 850 W/m° K.

In other examples, the material 50 could be otherwise disposed on the clamps 48. The material 50 could be combined with other materials to thereby form a composite material of the clamps 48. The material 50 could be disposed internally, but not externally, on the clamps 48. The clamps 48 could be made exclusively, or substantially exclusively, of the material 50. Thus, the scope of this disclosure is not limited to any particular manner of disposing the material 50 on, or incorporating the material in, the clamps 48.

One or more clamps 48 can be used to closely secure the optical line 44 to areas that may be most susceptible to leakage, such as, a connector 52. If a leak occurs at the connector 52, the connector will be cooled by the escaping gaseous fuel 30, and the highly thermally conductive material 50 on the clamps 48 will ensure that the optical line 44 (and optical waveguide(s) therein) are also cooled.

To detect any localized cooling of the optical line 44 along the enclosure 46, an optical interrogator 54 is optically connected to an optical waveguide 56 of the optical line 44. In the FIG. 2 example, the interrogator 54 includes an optical source 58 (such as, a laser or a light emitting diode) and an optical detector 60 (such as, an opto-electric converter or photodiode).

The optical source 58 launches light (electromagnetic energy) into the waveguide 56, and light returned to the interrogator 54 is detected by the detector 60. Note that it is not necessary for the light to be launched into a same end of the optical waveguide 56 as an end via which light is returned to the interrogator 54.

Other or different equipment (such as, an interferometer or an optical time domain or frequency domain reflectometer) may be included in the interrogator 54 in other examples. The scope of this disclosure is not limited to use of any particular type or construction of optical interrogator.

A computer 62 is used to control operation of the interrogator 54, and to record measurements made by the interrogator. In this example, the computer 62 includes at least a processor 64 and memory 66. The processor 64 operates the optical source 58, receives measurement data from the detector 60 and manipulates that data. The memory 66 stores instructions for operation of the processor 64, and stores processed measurement data. The processor 64 and memory 66 can perform additional or different functions in keeping with the scope of this disclosure.

In other examples, different types of computers may be used, the computer 62 could include other equipment (such as, input and output devices, etc.). The computer 62 could be integrated with the interrogator 54 into a single instrument. Thus, the scope of this disclosure is not limited to use of any particular type or construction of computer.

The optical line 44, interrogator 54 and computer 62 may comprise a distributed temperature sensing (DTS) system capable of detecting temperature as distributed along the optical waveguide 56. For example, the interrogator 54 could be used to measure a ratio of Stokes and anti-Stokes components of Raman scattering in the optical waveguide 56. In other examples, Brillouin scattering may be detected as an indication of temperature as distributed along the optical waveguide 56.

In further examples, fiber Bragg gratings 68 could be closely spaced apart along the optical waveguide 56, so that temperature changes will result in changes in light reflected back to the interrogator 54. An interferometer (not shown) may be used to detect such changes in the reflected light.

Such distributed temperature sensing (DTS) systems are well known to those skilled in the art, and so are not further described herein. However, it should be clearly understood that any optical system capable of detecting temperature changes along the optical line 44 may be used, in keeping with the principles of this disclosure.

Note that the optical line 44 can beneficially be the same as, or optically connected to, the optical line 26 positioned in the wellbore 18 in the FIG. 1 system 10. In this manner, the same interrogator 54 can be used to monitor fluid 14 flow in the well as is used to detect possible gas leakage at the wellsite. The optical waveguide 56 can extend to multiple locations, and/or multiple optical waveguides can be connected to the interrogator 54.

Although in the above examples the leakage detection system 42 is described as being used in conjunction with one or more pumps 12 for pumping fluid 14 into the wellbore 18, gas leakage can be detected by the system in other circumstances. Thus, the scope of this disclosure is not limited to use of the system 42 with fluid pumps at a wellsite.

Figure 3:
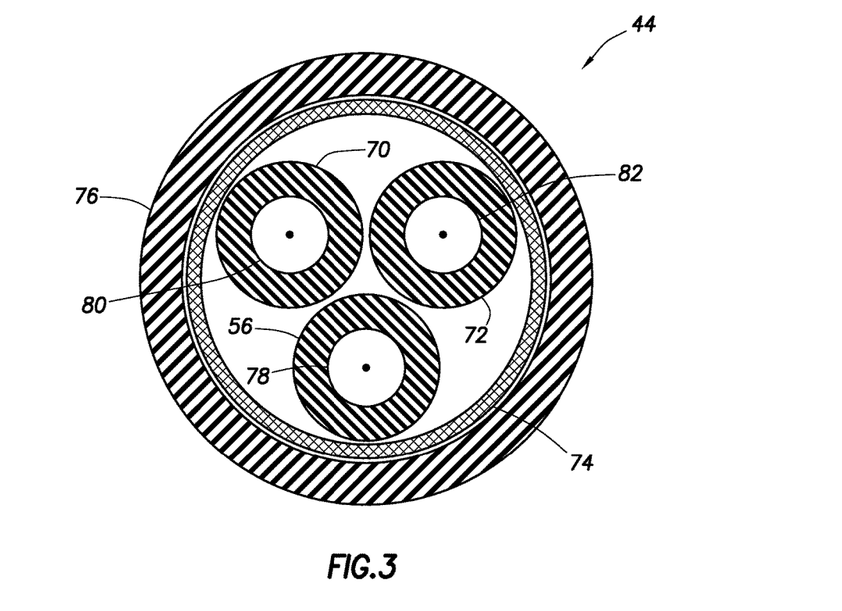
FIG. 3 is an enlarged scale representative cross-sectional view of an optical line that may be used in the system and method of FIG. 2.

Referring additionally now to FIG. 3, an enlarged scale cross-sectional view of one example of the optical line 44 is representatively illustrated. The optical line 44 may be used in the gaseous fuel monitoring system 42 and method of FIG. 2, or it may be used in other systems and methods.

In the FIG. 3 example, the optical line 44 includes the optical waveguide 56, as well as two additional optical waveguides 70, 72. The optical waveguides 56, 70, 72 are enclosed by a strength member 74 and an outer jacket 76.

In other examples, fewer or greater numbers of optical waveguides may be used, and the optical line 44 could be otherwise constructed. The strength member 74 may be made of a KEVLAR™ material, and the outer jacket 76 may be made of a polyurethane material, but other materials may be used if desired. Thus, the scope of this disclosure is not limited to any particular details of the optical line 44 described herein or depicted in the drawings.

In the FIG. 3 example, the optical waveguide 56 comprises a multimode optical fiber 78, and the optical waveguides 70, 72 comprise single mode optical fibers 80, 82. The multimode optical fiber 78 is used for distributed temperature sensing (DTS). The single mode optical fiber 80 is used for distributed acoustic sensing (DAS) and/or distributed strain sensing (DSS). The single mode optical fiber 82 can have the Bragg gratings 68 (see FIG. 2) formed therein, and can be used for distributed temperature, strain and/or acoustic sensing. However, it should be clearly understood that the scope of this disclosure is not limited to use of any particular type(s) of optical waveguides, or to any particular sensing technique(s) performed with the optical waveguides.

The optical waveguides 56, 70, 72 may be connected to the same optical interrogator 54 (see FIG. 2), for example, using an optical switch or wavelength division multiplexing (not shown) to individually or separately interrogate the different waveguides. In other examples, the waveguides 56, 70, 72 may be connected to separate interrogators 54.

One or more distributed optical sensing techniques may be performed using the optical line 44. These techniques can include detection of Brillouin scattering and/or coherent Rayleigh scattering resulting from transmission of light through the optical waveguides 56, 70, 72. Raman scattering may be detected and, if used in conjunction with detection of Brillouin scattering, may be used for thermally calibrating the Brillouin scatter detection data in situations, for example, where accurate strain measurements are desired.

Optical sensing techniques can be used to detect static strain, dynamic strain, acoustic vibration and/or temperature. These optical sensing techniques may be combined with any other optical sensing techniques, such as hydrogen sensing, stress sensing, etc.

Stimulated Brillouin scatter detection can be used to monitor strain and/or temperature along an optical waveguide. Coherent Rayleigh scatter can be detected as an indication of vibration of an optical waveguide, and/or as an indication of acoustic energy reaching the optical waveguide.

One or more waveguides may be used with Brillouin scatter detection, depending on the Brillouin method used (e.g., linear spontaneous or non-linear stimulated). The Brillouin scattering detection technique measures the temperature and/or strain via corresponding scattered photon frequency shift in a waveguide at a given location along the waveguide.

Coherent Rayleigh scatter detection can be used to monitor dynamic strain (e.g., acoustic pressure and vibration). Coherent Rayleigh scatter detection techniques can detect acoustic signals which result in vibration of an optical waveguide.

Raman scatter detection techniques are preferably used for monitoring distributed temperature. Raman scatter is relatively insensitive to distributed strain, although localized bending in a waveguide can be detected. Temperature measurements obtained using Raman scatter detection techniques can, for example, be used for temperature calibration of Brillouin scatter measurements.

Raman light scattering is caused by thermally influenced molecular vibrations. Consequently, the scattered light carries the local temperature information at the point where the scattering occurred.

The amplitude of an Anti-Stokes component is strongly temperature dependent, whereas the amplitude of a Stokes component of the backscattered light is not. Raman scatter sensing requires some optical-domain filtering to isolate the relevant optical frequency (or optical wavelength) components, and is based on the recording and computation of the ratio between Anti-Stokes and Stokes amplitude, which contains the temperature information.

Since the magnitude of the spontaneous Raman scattered light is quite low (e.g., 10 dB less than Brillouin scattering), high numerical aperture (high NA) multimode optical waveguides are typically used, in order to maximize the guided intensity of the backscattered light. However, the relatively high attenuation characteristics of highly doped, high NA, graded index multimode waveguides, in particular, limit the range of Raman-based systems to approximately 10 km.

Brillouin light scattering occurs as a result of interaction between a propagating optical signal and thermally excited acoustic waves (e.g., within the GHz range) present in silica optical material. This gives rise to frequency shifted components in the optical domain, and can be seen as the reflection of light from a dynamic in situ "virtual" optical grating generated by an acoustic wave within the optical media. Note that an acoustic wave is actually a pressure wave which introduces a modulation of the index of refraction via an elasto-optic effect.

The Brillouin reflected experiences a Doppler shift, since the grating propagates at the acoustic velocity in the optical media. The acoustic velocity is directly related to the silica media density, which is temperature and strain dependent. As a result, the so-called Brillouin frequency shift carries with it information about the local temperature and strain of the optical media.

Note that Raman and Brillouin scattering effects are associated with different fundamental physical properties of silica optical media and, therefore, have completely different spectral characteristics.

Coherent Rayleigh light scattering is also caused by fluctuations or non-homogeneities in silica optical media density, but this form of scattering is purely "elastic." In contrast, both Raman and Brillouin scattering effects are "inelastic," in that "new" wavelengths of light are generated from the light propagating through the media.

In the case of coherent Rayleigh light scattering, temperature or strain effects do not induce wavelength changes. Unlike conventional Rayleigh scatter detection techniques (using common optical time domain reflectometers), because of the extremely narrow spectral width of the optical source (with associated long coherence length and time), coherent Rayleigh (or phase Rayleigh) scatter signals experience optical phase sensitivity resulting from coherent addition of amplitudes of the light scattered from different parts of the optical media which arrive simultaneously at a photo-detector.

Figure 4:
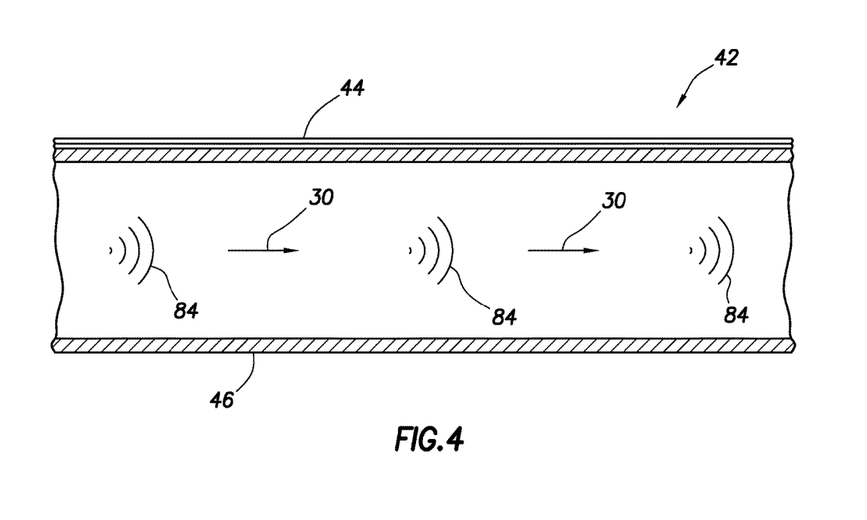
FIG. 4 is a cross-sectional view of a gas enclosure in the system and method of FIG. 2.

Referring additionally now to FIG. 4, a cross-sectional view of the enclosure 46 in the monitoring system 42 is representatively illustrated, with the optical line 44 positioned adjacent the enclosure. In this example, the optical line 44 of FIG. 3 is used, but other optical lines may be used in other examples.

Although not shown in FIG. 4, the clamps 48 (see FIG. 2) can be used to secure the optical line 44 along the enclosure 46. The optical line 44 can, thus, be exposed to acoustic vibrations, pressure pulses, strains, temperature changes, etc., experienced by the enclosure 46. Of course, other ways of securing the optical line 44 to the enclosure 46 may be used, if desired.

It is known that an acoustic "signature" (frequency components, amplitude, etc.) of a gas flow is related to various parameters of the gas flow. See, for example, S. L. Garrett, "Sonic Gas Analysis," ETHOS2009 Conference Proceedings, Kirkland, Wash., USA, 23-25 Jan. 2009.

Thus, changes in composition and flow rate (or velocity) of the gaseous fuel 30 in the enclosure 46 can be detected by monitoring the acoustic signature of the flow of the fuel through the enclosure. For example, a change in the gas composition should produce a corresponding change in the frequency of the acoustic signature, and a change in the gas composition flow rate should produce a corresponding change in the amplitude of the acoustic signature.

The DAS (distributed acoustic sensing) or dynamic DSS (distributed strain sensing) techniques described above can be used to detect the acoustic signature. Acoustic vibrations, pressure pulses and/or dynamic strains experienced by the optical waveguides 56, 70, 72 will, thus, result in changes in optical backscatter in the optical waveguides and/or changes in reflections from the Bragg gratings 68 (for example, using an array of the Bragg gratings as a series of Fabry-Perot interferometers), which changes can be detected by the interrogator 54.

Alternatively, or in addition, the flow rate (or velocity) of the gaseous fuel 30 through the enclosure 46 can be determined by tracking one or more acoustic or pressure signals 84 propagating in the gaseous fuel. The signals 84 can be generated, for example, using piezoelectric actuators, mechanical strikers or modulated valves (not shown) in or along the enclosure 46.

The signals 84 may be generated periodically, or only when desired to detect the parameters of the gaseous fuel 30 flow. The signals 84 may be propagated in a same direction as the flow and/or in an opposite direction.

A velocity of the signals 84 through the enclosure 46 depends on an acoustic velocity of the gaseous fuel 30 (and is, thus, related to the composition of the gaseous fuel), and on the velocity of the gaseous fuel through the enclosure. Therefore, changes in composition and/or flow rate of the gaseous fuel 30 can be detected by monitoring the propagation of the signals 84 through the enclosure 46.

The DAS or dynamic DSS techniques described above can be used to track the propagation of the signals 84 through the enclosure 46. Acoustic vibrations, pressure pulses and/or dynamic strains experienced by the optical waveguides 56, 70, 72 will, thus, result in changes in optical backscatter in the optical waveguides and/or changes in reflections from the Bragg gratings 68 (for example, using an array of the Bragg gratings as a series of Fabry-Perot interferometers), which changes can be detected by the interrogator 54.

A leakage of the gaseous fuel 30 from the enclosure 46 will produce an acoustic signal that can be detected using the DAS techniques described above. Strains in the enclosure 46 (for example, resulting from excessive bending of a gas line, damage to an enclosure, etc.) can be detected using the DSS techniques described above.

It may now be appreciated that the above disclosure provides significant advancements to the arts of constructing and operating wellsite detection systems. In examples described above, the optical line 44 can be used to efficiently and effectively detect any leakages of the gaseous fuel 30 from the enclosure 46, to determine parameters of the gaseous fuel flow, and to detect changes in the composition of the gaseous fuel. Use of the optical line 44 is intrinsically safe, in that it does not require any electrical or other spark generating equipment in close proximity to the gaseous fuel 30 or other potentially hazardous wellsite location.

A gaseous fuel monitoring system 42 for use with a subterranean well is provided to the art by the above disclosure. In one example, the system 42 comprises a gaseous fuel supply enclosure 46, an optical line 44 extending along the gaseous fuel supply enclosure 46, and a relatively highly thermally conductive material 50 contacting both the gaseous fuel supply enclosure 46 and the optical line 44.

The relatively highly thermally conductive material 50 may comprise a pyrolytic carbon material. The pyrolytic carbon material can be disposed on a clamp 48 which secures the optical line 44 to the gaseous fuel supply enclosure 46.

The gaseous fuel supply enclosure 46 may comprise a gas line 36, 38, 40 connecting a motor 28 to a gaseous fuel supply tank 32.

The optical line 44 can be optically connected to an optical interrogator 54. At least one of Raman, Brillouin and coherent Rayleigh optical scattering may be detected by the optical interrogator 54. Temperature as distributed along the optical line 44 can be detected.

A method of detecting leakage from a gaseous fuel supply enclosure 46 is also described above. In one example, the method can include: securing an optical line 44 to the gaseous fuel supply enclosure 46, the securing step comprising contacting a pyrolytic carbon material with the optical line 44 and the gaseous fuel supply enclosure 46.

The method can include detecting temperature as distributed along the gaseous fuel supply enclosure 46.

The detecting step can include connecting the optical line 44 to an optical interrogator 54.

The detecting step can include detecting at least one of Raman and Brillouin optical scattering.

The detecting step can include detecting reflections of light from fiber Bragg gratings 68.

The pyrolytic carbon material may be disposed on or in a clamp 48 which secures the optical line 44 to the gaseous fuel supply enclosure 46.

Another gaseous fuel monitoring system 42 described above can comprise: a gaseous fuel supply enclosure 46, an optical line 44 extending along the gaseous fuel supply enclosure 46, and a pyrolytic carbon material contacting both the gaseous fuel supply enclosure 46 and the optical line 44.

The optical line 44, 26 can extend into a wellbore 18.

Another gaseous fuel monitoring system 42 for use with a subterranean well is described above. In one example, the system 42 can comprise: a gaseous fuel supply enclosure 46 disposed proximate the earth's surface; an optical line 44 extending along the gaseous fuel supply enclosure 46 proximate the earth's surface; and an optical interrogator 54 connected to the optical line 44, wherein the optical interrogator 54 detects changes in light transmitted by the optical line 44, the changes in the light transmitted by the optical line 44 being due to changes in vibrations of the enclosure 46.

The vibrations may correspond to an acoustic signature of gaseous fuel 30 flow through the enclosure 46.

The changes in the vibrations can result from changes in at least one parameter of gaseous fuel 30 flow through the enclosure 46. The parameter may be gas composition and/or flow rate.

The vibrations may correspond to at least one acoustic and/or pressure signal 84 propagated through the enclosure 46.

Although various examples have been described above, with each example having certain features, it should be understood that it is not necessary for a particular feature of one example to be used exclusively with that example. Instead, any of the features described above and/or depicted in the drawings can be combined with any of the examples, in addition to or in substitution for any of the other features of those examples. One example's features are not mutually exclusive to another example's features. Instead, the scope of this disclosure encompasses any combination of any of the features.

Although each example described above includes a certain combination of features, it should be understood that it is not necessary for all features of an example to be used. Instead, any of the features described above can be used, without any other particular feature or features also being used.

It should be understood that the various embodiments described herein may be utilized in various orientations, such as inclined, inverted, horizontal, vertical, etc., and in various configurations, without departing from the principles of this disclosure. The embodiments are described merely as examples of useful applications of the principles of the disclosure, which is not limited to any specific details of these embodiments.

In the above description of the representative examples, directional terms (such as "above," "below," "upper," "lower," etc.) are used for convenience in referring to the accompanying drawings. However, it should be clearly understood that the scope of this disclosure is not limited to any particular directions described herein.

The terms "including," "includes," "comprising," "comprises," and similar terms are used in a non-limiting sense in this specification. For example, if a system, method, apparatus, device, etc., is described as "including" a certain feature or element, the system, method, apparatus, device, etc., can include that feature or element, and can also include other features or elements. Similarly, the term "comprises" is considered to mean "comprises, but is not limited to."

Of course, a person skilled in the art would, upon a careful consideration of the above description of representative embodiments of the disclosure, readily appreciate that many modifications, additions, substitutions, deletions, and other changes may be made to the specific embodiments, and such changes are contemplated by the principles of this disclosure. For example, structures disclosed as being separately formed can, in other examples, be integrally formed and vice versa. Accordingly, the foregoing detailed description is to be clearly understood as being given by way of illustration and example only, the spirit and scope of the invention being limited solely by the appended claims and their equivalents.

What is claimed is:

1. A gaseous fuel monitoring system for use with a subterranean well, the system comprising:
    a gaseous fuel supply enclosure comprising a connector;
    an optical line extending along the gaseous fuel supply enclosure across the connector and secured by at least one clamp,
    wherein the clamp comprises a highly thermally conductive material having a conductivity of at least 850 Watts per meters Kelvin (W/m*K) contacting both the connector and the optical line; and
    an optical interrogator in communication with the optical line to monitor the gaseous fuel supply enclosure by detecting a change in temperature of the clamp.

2. The system of claim 1, wherein the highly thermally conductive material comprises a pyrolytic carbon material.

3. The system of claim 1, wherein the gaseous fuel supply enclosure comprises a gas line connecting a motor to a gaseous fuel supply tank.

4. The system of claim 1, wherein at least one of Raman, Brillouin and coherent Rayleigh optical scattering is detected by the optical interrogator.

5. The system of claim 1, wherein the clamp is internally coated with the highly thermally conductive material having a conductivity of at least 850 Watts per meters Kelvin (W/m*K).

6. The system of claim 1, wherein the change in temperature of the clamp results from a gaseous leak at the connector due to the Joule Thompson effect.

7. The system of claim 6, wherein the gaseous leak comprises methane.

8. A method of detecting leakage from a gaseous fuel supply enclosure, the method comprising:
    securing an optical line along the gaseous fuel supply enclosure and across a connector of the gaseous fuel supply enclosure, the securing comprising a clamp comprising a pyrolytic carbon material contacting the optical line and the connector; and
    detecting a leak from the enclosure by detecting a change in temperature of the clamp via an optical interrogator in communication with the optical line.

9. The method of claim 8, wherein the detecting comprises detecting at least one of Raman, Brillouin and coherent Rayleigh optical scattering.

10. The method of claim 8, wherein the gaseous fuel supply enclosure comprises a gas line connecting a motor to a gaseous fuel supply tank.

11. The method of claim 8, wherein the clamp is internally coated with the pyrolytic carbon material.

12. The method of claim 8, wherein the change in temperature of the clamp results from a gaseous leak at the connector due to the Joule Thompson effect.

13. The method of claim 12, wherein the gaseous leak comprises methane.

14. A gaseous fuel monitoring system, the system comprising:
    a gaseous fuel supply enclosure disposed proximate the earth's surface, the gaseous fuel supply enclosure comprises a connector;
    an optical line extending along the gaseous fuel supply enclosure and across the connector proximate the earth's surface;
    a clamp comprising a highly thermally conductive material having a conductivity of at least 850 Watts per meters Kelvin (W/m*K) contacting both the connector and the optical line; and
    an optical interrogator in communication with the optical line to monitor the gaseous fuel supply enclosure by detecting a change in temperature of the clamp.

15. The system of claim 14, wherein the clamp which secures the optical line to the gaseous fuel supply enclosure comprises a pyrolytic carbon material.

16. The system of claim 14, wherein the gaseous fuel supply enclosure comprises a gas line connecting a motor to a gaseous fuel supply tank.

17. The system of claim 14, wherein at least one of Raman, Brillouin and coherent Rayleigh optical scattering is detected by the optical interrogator.

18. The system of claim 14, wherein the clamp is internally coated with the highly thermally conductive material having a conductivity of at least 850 Watts per meters Kelvin (W/m*K).

19. The system of claim 14, wherein the change in temperature of the clamp results from a gaseous leak at the connector due to the Joule Thompson effect.

20. The system of claim 19, wherein the gaseous leak comprises methane.

* * * * *